(12) United States Patent
Edvardsson

(10) Patent No.: US 9,410,904 B2
(45) Date of Patent: Aug. 9, 2016

(54) SYSTEM AND METHOD FOR DETERMINING DENSITY OF A MEDIUM IN A TANK

(71) Applicant: Rosemount Tank Radar AB, Gothenburg (SE)

(72) Inventor: Olov Edvardsson, Linkoping (SE)

(73) Assignee: ROSMOUNT TANK RADAR AB, Gothenburg (SE)

( * ) Notice: Subject to any disclaimer, the term of this patent is extended or adjusted under 35 U.S.C. 154(b) by 99 days.

(21) Appl. No.: 14/138,522

(22) Filed: Dec. 23, 2013

(65) Prior Publication Data

US 2015/0177163 A1  Jun. 25, 2015

(51) Int. Cl.
*G01N 22/00* (2006.01)
*G01N 9/24* (2006.01)
*G01F 23/284* (2006.01)

(52) U.S. Cl.
CPC .............. *G01N 22/00* (2013.01); *G01F 23/284* (2013.01); *G01N 9/24* (2013.01)

(58) Field of Classification Search
CPC ..... E21B 17/028; E21B 47/12; E21B 17/003; E21B 41/0085
USPC ....................................... 324/642, 27, 51, 44
See application file for complete search history.

(56) References Cited

U.S. PATENT DOCUMENTS

| | | | |
|---|---|---|---|
| 2002/0000316 A1* | 1/2002 | Haase | 166/244.1 |
| 2009/0289808 A1* | 11/2009 | Prammer | 340/853.7 |
| 2012/0176138 A1* | 7/2012 | Prammer | 324/338 |
| 2013/0137110 A1 | 5/2013 | Kraihanzel | |
| 2014/0277920 A1* | 9/2014 | Raniere | 701/32.8 |

FOREIGN PATENT DOCUMENTS

| | | |
|---|---|---|
| DE | 101 36 754 | 2/2003 |
| EP | 0 789 237 | 8/1997 |
| EP | 1 623 764 | 8/2006 |
| JP | 2011-221025 | 11/2011 |
| NO | 331262 | 11/2011 |
| WO | WO 2006/084263 | 8/2006 |

OTHER PUBLICATIONS

Notification of Transmittal of the International Search Report and the Written Opinion of the International Searching Authority, PCT/EP2014/078254, dated Mar. 19, 2015.

* cited by examiner

*Primary Examiner* — Tung X Nguyen
*Assistant Examiner* — Zannatul Ferdous
(74) *Attorney, Agent, or Firm* — Westman, Champlin & Koehler, P.A.

(57) ABSTRACT

A system and method for determining a density of a non-conducting medium in a tank is disclosed where the relationship between a dielectric constant and a density of the medium is known. The system comprises a transceiver, and a waveguide, the waveguide extends towards and into the medium. The system further comprises a first microwave resonator located along the waveguide. The first microwave resonator has a resonance frequency, which depends on a dielectric constant of a medium surrounding the resonator according to a known relationship, and is arranged to reflect a portion in the frequency domain of a signal being guided along the waveguide. The system further comprises processing circuitry connected to the transceiver and configured to determine the resonance frequency based on a received reflected signal, and to determine a density of the medium at the location of the first microwave resonator based on the resonance frequency.

29 Claims, 8 Drawing Sheets

SYSTEM AND METHOD FOR DETERMINING DENSITY OF A MEDIUM IN A TANK

FIELD OF THE INVENTION

The present invention relates to a system and a method for determining a density of a medium in a tank using electromagnetic waves.

TECHNICAL BACKGROUND

Radar level gauges are in wide use for measuring process variables of a product contained in a tank, such as filling level, temperature, pressure etc. Radar level gauging is generally performed either by means of non-contact measurement, whereby electromagnetic signals are radiated towards the product contained in the tank, or by means of contact measurement, often referred to as guided wave radar (GWR), whereby electromagnetic signals are guided towards the product by a probe acting as a waveguide. The probe is generally arranged vertically from top to bottom of the tank. The electromagnetic signals are subsequently reflected at the surface of the product, and the reflected signals are received by a receiver or transceiver comprised in the radar level gauge system. Based on the transmitted and reflected signals, the distance to the surface of the product can be determined.

In many applications, it is also desirable to be able to measure the density of a product in a tank in order to further improve the accuracy during custody transfers. Due to the large amount being transferred during custody transfers, a small measurement error will incur large economical costs. Another desire is to survey a possible vertical stratification of the density. In tanks for liquid gas (LNG, LPG etc.) suck stratification might create unstable conditions. A number of density measurements at different heights are needed to provide that information.

WO2006084263 discloses a system for sensing, monitoring and evaluating properties of fluids used in fluid systems. In particular, mechanical resonators are arranged at multiple positions within the fluid system. The mechanical resonators can be actively stimulated by an external signal and the response from the resonators can be used to determine for example the density of the product in which a resonator is located. The mechanical resonators are specified to resonate in the kHz to MHz range, and are configured as tuning forks to vibrate at a resonance frequency to determine properties in the fluidic system.

However, mechanical resonators are very sensitive to contamination, i.e. if a contaminant is attached to a tuning fork-type resonator, the resonance frequency of the resonator may change due to the additional mass of the resonator, which in turn may lead to an erroneous determinations of a property of the fluid. Accordingly, it is desirable to provide an improved system for determining properties of a product kept in a tank.

SUMMARY OF THE INVENTION

In view of the above-mentioned, a general object of the present invention is to provide an improved system and method for determining the density of a product in a tank. Another object is to also measure a filling level with the improved system, thus providing one system for measuring at least two process variables.

According to a first aspect of the present invention, there is provided a system for determining a density of a non-conducting medium in a tank, where a relationship between a dielectric constant and a density of the medium is known. The system comprises a transceiver configured to generate, transmit and receive a microwave electromagnetic signal comprising frequencies within a predetermined frequency range, and a waveguide connected to the transceiver and extending towards and into the medium and arranged to guide a transmitted electromagnetic signal towards and into the medium inside the tank, and to return an electromagnetic signal resulting from a reflection of the transmitted electromagnetic signal. The system further comprises a first microwave resonator which has a resonance frequency, and is configured to reflect frequencies corresponding to a first bandwidth around the resonance frequency, the first bandwidth being smaller than and within the frequency range, and the resonance frequency depending on a dielectric constant of a medium surrounding the resonator according to a known relationship. The first microwave resonator is arranged at a location along the waveguide, and is configured to reflect a portion in the frequency domain of an electromagnetic signal corresponding to the first bandwidth when the electromagnetic signal is guided along the waveguide. There is processing circuitry which is connected to the transceiver and configured to determine the resonance frequency based on a reflected portion of a received signal having been reflected by the first microwave resonator, the processing circuitry being further configured to determine a density of the medium at the location of the first microwave resonator based on the resonance frequency.

The "transceiver" may be one functional unit capable of generating, transmitting and receiving microwave electromagnetic signals, or it may be a system comprising separate transmitter and receiver units. The transceiver is capable of generating and transmitting a microwave electromagnetic signal which may be stepped or swept over a predetermined frequency range in which the resonance frequency of the resonator is expected.

In the context of the present application, the waveguide is designed for guiding electromagnetic signals. Several types of waveguides, for example single-line (Goubau- or Sommerfeld-type), and twin-line probes may be used. The probes may be essentially rigid or flexible and they may be made from metal, such as stainless steel, plastic, such as PTFE, or a combination thereof.

The tank may be any container or vessel capable of containing a product, and may be metallic, or partly or completely non-metallic, open, semi-open, or closed. For some applications in tanks containing LNG (Liquefied Natural Gas e.g. methane) or LPG (Liquefied Petroleum Gas e.g. propane, butane etc.), the tanks have good temperature insulation, due to LNG in some cases being transported at −163° C., or with enclosures withstanding high pressures such as 15-20 bar in the case of LPG.

The microwave resonator should be understood to be located at any position along the waveguide, such that a portion of the signal propagating along the probe is reflected when the signal pass the position of the resonator. The microwave resonator has a resonance frequency which has a first bandwidth, the first bandwidth being smaller than and within the frequency range. By the first bandwidth being smaller and within the frequency range it should be understood that the first bandwidth comprises a portion of the frequencies i.e. a range of frequencies within the frequency range. The resonance frequency being dependent on a dielectric constant of a medium surrounding the microwave resonator according to a known relationship should be understood as that due to design i.e. shape and form, tests and/or prior calculations, the microwave resonator is configured to exhibit a known resonance frequency at known dielectric constants. This known resonance frequency could be either a function of the dielectric constant, i.e. that there is a continuous known relationship, or that a sufficient number of discrete data points are known such that all resonance frequencies may be fitted to the corresponding data points according to values of the dielectric constant of the surrounding medium. Thereby, by determining the resonance frequency it is possible to determine the dielectric constant. For many cases it is advantageous if the resonance frequency decreases with an increasing dielectric constant, for example a resonance frequency which varies according to the inverse square root of the dielectric constant of the surrounding medium.

By being arranged to reflect a portion of the signal in the frequency domain corresponding to the first bandwidth when the signal is being guided by the waveguide, it should be understood that the microwave resonator is coupled to the waveguide and a transmitted signal passing a resonator along the waveguide will excite the resonator. The coupling between the microwave resonator and the waveguide is weak in order to enable the first bandwidth, i.e. the bandwidth of the resonator, to be small, and concurrently enable the microwave resonator to reflect portions of signals within the first bandwidth. The first bandwidth in which the microwave resonator can be excited may be estimated as $f_0/Q$, $f_0$ being the resonance frequency and Q being the Q-value of the microwave resonator including the coupling to the waveguide. Low resistive losses and a weak coupling to the waveguide will provide a high Q-value, e.g. 1000 or more. If a signal comprises a frequency or frequencies far away from the actual resonance frequency, which is dependent on the dielectric constant of the medium surrounding the microwave resonator, the signal will only cause a small excitation of the microwave resonator, and the microwave resonator will have an negligible influence on the signal being guided along the waveguide when passing the microwave resonator. A signal comprising a frequency closer to the resonance frequency of the microwave resonator, such as a signal comprising a frequency or frequencies within the first bandwidth, will cause a larger excitation and will thus have a higher influence on the signal passing the microwave resonator. A larger excitation of the resonator will cause more power to be "taken" from the signal, and a portion of the signal will consequently be absorbed by losses in the microwave resonator. The remaining, non-absorbed, signal will be divided into two parts, a reflected portion which is guided back towards the transceiver, and a transmitted portion which continues along the waveguide. The transmitted part of the signal may be reflected further away from the transceiver by an impedance transition and a part of that reflection will return to the transceiver after leaving some power at the resonator a second time.

The microwave resonator is preferably designed having a high Q-value, i.e. the relationship between the resonance frequency and the half power bandwidth. The reflection from such a microwave resonator is comprised in a narrow frequency band e.g. the first bandwidth and is thus easily distinguished from a reflection resulting from an impedance transition such as a surface of a product kept in the tank, as such a surface reflects signals of a broad band of frequencies. The preferably high Q-value requires that some, or all parts of the microwave resonator are made of good conductors or plated by a conducting material such as gold. Furthermore, the surrounding medium, e.g. a liquid, preferably has low dielectric losses, such as tan δ<0.001, to provide a narrow-band resonance.

The reflected portion of the signal reaching the transceiver will comprise frequencies of the first bandwidth, thus indicating the resonance frequency. A microwave resonator above a surface of a medium in a tank therefore has a different reflected resonance frequency compared to a microwave resonator which is immersed in a non-conducting medium.

It can be assumed that the dielectric constant of a particular material has a known relation to the density of the material, and the density can therefore be derived from determining the dielectric constant. Furthermore, by appropriately designing the microwave resonator, the relationship between the resonance frequency and the dielectric constant of the material with which it is in contact can be determined theoretically, thereby providing a known relation between the resonance frequency and density. Accordingly, a possibility to measure the density through a determination of the resonance frequency of a microwave resonator is provided. An advantage, for example in comparison to mechanical resonators, is that no moving parts are present, which will make the system according to the present invention more robust and possibly alleviate the need for maintenance.

The processing circuitry is connected to the transceiver and configured to determine the resonance frequency of the microwave resonator, based on a received reflected electromagnetic signal comprising an indication of a resonance frequency of a microwave resonator, the indication typically being a reflected portion of the received electromagnetic signal. Furthermore, the processing circuitry is configured to determine the density of the medium at the location of the microwave resonator based on the known relationship between the resonance frequency of the microwave resonator and the dielectric constant of the non-conducting medium. The relation between the dielectric constant and the density of a material can for example be estimated theoretically within a relevant temperature interval, or it may be known from empirical studies.

There are a number of typical applications of the present invention, where non-conducting mediums are transported, e.g. LNG (methane or ethane stored at low temperature) or LPG (propane, butane etc. usually stored under pressure) but other hydrocarbons or liquids having low dielectric losses can be measured as well.

The present invention is thus based on the realization that it is possible to determine the density of a product in a system by using a microwave resonator which is configured such that the microwave resonator has a resonance frequency which is dependent on the density of a medium in which the microwave resonator is immersed. The resonance frequency will be dependent on the dielectric constant of the medium surrounding the microwave resonator, and the dielectric constant for the non-conducting mediums which are to be measured with the present invention is dependent on the density. Thereby, the density of the product can accurately be determined.

According to one embodiment of the invention the frequency range is at least two times greater than said first bandwidth. To facilitate the distinction between the narrow-band reflection resulting from reflection of frequencies comprised in the first bandwidth from the microwave resonator from other reflections along the waveguide, the frequency range is preferably larger, and at least two times larger than the first bandwidth. The frequency range may also be greater than two times the first bandwidth, such as an order of magnitude or even two or three orders of magnitude greater to even further distinguish the reflected portion.

According to another embodiment of the invention the first bandwidth may be approximately 1 MHz or less. A bandwidth in the order of approximately 1 MHz or less will provide a narrow-band reflection with a strong reflection. A smaller bandwidth e.g. 0.5 MHz or smaller may further facilitate the determination of the resonance frequency. However, a smaller bandwidth will also require a higher Q-value for the microwave resonator. Hence, a smaller bandwidth is desirable but will also require a microwave resonator with a higher Q-value.

According to another embodiment of the invention, the medium may be a low viscosity liquid. Low viscosity liquids will easily flow around, surround and fill the microwave resonator and thus influence the density measurement.

According to one embodiment of the invention, the microwave resonator may be configured to have a higher resonance frequency at a lower dielectric constant of the medium surrounding the microwave resonator. By configuring the microwave resonator to exhibit a higher resonance frequency at a lower dielectric constant, it is for practical intents and purposes ensured that that highest resonance frequency is shown when the resonator is empty i.e. filled by tank atmosphere, since tank atmosphere has a dielectric constant close to one.

According to one embodiment of the invention the microwave resonator may be arranged at a distance from the waveguide such that a portion of the signal propagating along the waveguide is reflected when reaching a location of the resonator. An electromagnetic signal propagating along a waveguide will have a radial extension, which has a range which depends on the strength and frequency of the signal. The radial extension of the signal means that the signal will encounter interference when objects are within the range of the radial extension. Thus, by arranging the microwave resonator at a distance the interference caused by the microwave resonator may be reduced, while the radial extension of the signal will allow the microwave resonator to be excited and reflect a portion of the signal at a distance from the waveguide. Accordingly, the microwave resonator may be capacitively coupled to the waveguide, or as an alternative, the microwave resonator may be inductively coupled to waveguide. By capacitively or inductively coupling the microwave resonator to the waveguide no physical connections are needed to enable the microwave resonator to reflect portions of an electromagnetic signal traveling along the waveguide. Thus a reduced number of components are needed, and further no interference from e.g. a wiring connecting the waveguide and microwave resonator will be present.

According to one embodiment of the invention, the system further comprises a support structure arranged in the proximity of the waveguide and extending substantially in parallel with the waveguide, wherein the microwave resonator is arranged on the support structure. Arranging the microwave resonator on the support structure allows the microwave resonator to be mechanically decoupled from the waveguide, thus not adding any extra consideration when choosing or designing a waveguide for the system.

According to another embodiment of the invention, the system may further comprise a plurality of retaining elements arranged at fixed positions in relation to an inside of the tank and spaced apart along the waveguide, wherein each of the plurality of retaining elements is arranged to maintain a predetermined minimum distance between the waveguide and the microwave resonator. By keeping a predetermined minimum distance between the microwave resonator and the waveguide, no contact and thus damage or interaction between them will occur. Further, the distance will determine the strength of the capacitive coupling between the waveguide and the microwave resonator. Hence, the predetermined minimum distance may be set to determine a strong capacitive coupling while minimizing the interference caused by the microwave resonator. Accordingly, at least one of said plurality of retaining elements may be attached to the support structure.

For example, a tank for cryogenic methane (LNG) generally has a vertical "tower" in its middle where pumps, level gauging system, sensors for temperature and pressure etc. are attached. The tower is as high as the tank (30-45 m) and thus a very big and steady construction. During rough seas the moving liquid within the tank present a very big force on the tower and all parts on it. A waveguide may be mounted along such a tower. Depending on how the waveguide is constructed, attachments such as the above mentioned retaining elements may be necessary along the waveguide in order to stabilize and ensure that the waveguide does not break. The microwave resonators used by the present invention may then be attached to the tower (preferably close to the attachment points of the waveguide) with some electrical coupling to the waveguide. Alternatively, the microwave resonators are designed as rather slim devices which can be supported by the waveguide itself.

According to one embodiment of the invention, the microwave resonator may comprise a tubular housing having an open end, a closed end and an inner rod fixedly attached to the closed end. The inner rod extends along a central axis of the housing from the closed end towards the open end. Furthermore, the inner rod may have a length in the range of 25 to 40 mm. Further the tubular housing may be longer than the inner rod, such that the inner rod does not extend out of the open end of the tubular housing. The tubular housing may be cylindrical, and the tubular housing may have an inner diameter in the range of 10 to 20 mm. The given dimensions will result in a resonator having a resonance frequency, when filled with a dielectric medium, approximately in the range of 2-2.5 GHz. The microwave resonator may be substantially horizontally aligned, or the microwave resonator may be substantially vertically aligned having the open end arranged pointing in a downward direction. According to various embodiment of the present invention, the microwave resonator may comprise holes having a diameter less than 4 mm in the tubular housing. The holes will allow a surrounding liquid to more quickly enter and leave and thus fill the microwave resonator. The small size of the holes will enable them to perform this function without disturbing the measurements, since such small holes i.e. less than a tenth of the wavelength will have a very small negligible effect on the measurements.

According to another embodiment of the invention the system may further comprise a filling level determination circuitry configured to determine a filling level of a medium in the tank based on a time-of-flight between the transmitted signal and a received reflected electromagnetic signal reflected at a surface of the medium in the tank. the system for measuring density may advantageously also be used to detect and determine the filling level of the medium in the tank, thereby providing a system for measuring both the density and the filling level. Providing a combined measurement system may reduce the costs compared to if two separate systems must be used. Furthermore, the number of passages into the tank will be reduced compared to for two separate measurement systems, thus alleviating customer concerns about long and troublesome installation processes and reducing the complexity of the tank.

According to one embodiment of the invention, the system may further comprise a second microwave resonator having a second resonance frequency, and configured to reflect frequencies corresponding to a second bandwidth around the second resonance frequency. The second bandwidth being smaller than and within the frequency range, the second resonance frequency being separate from the resonance frequency of the first microwave resonator, and depending on a dielectric constant of a medium surrounding the second microwave resonator according to a known relationship. The second microwave resonator is arranged at a location along the waveguide offset from the first microwave resonator, and configured to reflect a portion in the frequency domain corresponding to the second bandwidth when the electromagnetic signal is guided along the waveguide. The processing circuitry is further configured to determine the second resonance frequency based on a reflected portion of a received signal having been reflected by the second microwave resonator, and to determine a density of the medium at the location of the second microwave resonator based on the second resonance frequency. For some products kept in a tank, stratification may occur where layers of the product at different densities are formed which may lower accuracy during custody transfer, or even confer a risk when a quick change in positions of the stratified layers occur. Therefore a measurement of the density at several locations along the waveguide provides an added accuracy and a safer system.

According to another embodiment of the invention the first microwave resonator may be configured to have a first resonance frequency range in a product having a known dielectric constant range, and the second microwave resonator is configured to have a second resonance frequency range in the product having the known dielectric constant range. The first resonance frequency range does not overlap the second resonance frequency range.

The known dielectric constant range may for example be the range of dielectric constants for different densities of a medium in a tank known to occur under certain circumstances. By resonance frequency range it should be understood that the first and second resonance frequency, due to varying dielectric constant of the medium surrounding said microwave resonators, are varying within this frequency range. Thus, separating the first resonance frequency range from the second resonance frequency range such that they do not overlap will ensure that each of the resonance frequencies i.e. the first and the second resonance frequency are detectable and do not interfere with each other. By not interfering with each other it should be understood that there is no possibility for a reflected portion of a signal to be misinterpreted as belonging to the first microwave resonator when in fact it belongs to the second microwave resonator and vice versa.

Accordingly, if the system comprises more than two resonators, all the resonators are configured with different resonance frequencies to enable a clear distinction between them, and when they are filled with a non-conducting medium the resonance will be within a known frequency band, for example 2-3 GHz. When the microwave resonators are empty they may have resonance which is higher. For example the resonance frequency may be approximately 40 percent higher when the microwave resonators are above the surface of the medium and filled by the tank atmosphere. Those "empty" resonance frequencies may or may not be measurable depending on the application of the system, for instance, verification or information of a non-immersed state may be used to ensure that a filling level is below a certain microwave resonator in applications where safety concerns are very important. If the same system is being used for level gauging, i.e. filling level determination, a lower frequency band may be used for level gauging, for example 1-2 GHz, and by that separation no interference should occur between level gauging and density measurement.

According to various embodiments of the invention the frequency of the transmitted electromagnetic signal may be in the range of 1 to 3 GHz. Providing an electromagnetic signal which extends in a relatively large frequency range compared to the bandwidth of the frequency range in which the microwave resonators reflects signals allows for an easy detection of the reflected frequencies since they are easily distinguished as reflected portions of the electromagnetic signal. Hence, the reflected frequencies are easily detected compared to the rest of the spectrum of the electromagnetic signal. Further, a portion corresponding to a sub-range of the frequency range of the signal may be used to determine density, and another portion may be used to determine the filling level as described above.

According to one embodiment of the invention the non-conducting medium may be either liquid petroleum gas (LPG) or liquid natural gas (LNG). Both LPG and LNG are non-conducting mediums which are transported in marine tanks where both filling level for custody transfer operations and hence also density measurement are important considerations for determining the accuracy of the custody transfer.

According to a second aspect of the invention, there is also provided a method for determining a density of a non-conducting medium in a tank, where a relationship between a dielectric constant and a density of the medium is known. The method may be performed in a system comprising a transceiver configured to generate, transmit and receive a microwave electromagnetic signal comprising frequencies within a predetermined frequency range, and a waveguide connected to the transceiver and extending towards and into the medium, arranged to guide a transmitted electromagnetic signal towards and into the medium inside the tank, and to return an electromagnetic signal resulting from a reflection of the transmitted electromagnetic. The system further comprises a first microwave resonator having a resonance frequency, and configured to reflect frequencies corresponding to a first bandwidth around the resonance frequency, the first bandwidth being smaller than and within the frequency range, the resonance frequency depending on a dielectric constant of a medium surrounding the resonator according to a known relationship. The first microwave resonator is arranged at a location along the waveguide, and configured to reflect a portion in the frequency domain, of an electromagnetic signal corresponding to the first bandwidth when the electromagnetic signal is guided along the waveguide. The system further comprises processing circuitry connected to the transceiver and configured to determine the resonance frequency based on a reflected portion of the signal having been reflected by the first microwave resonator, and to determine a density of the medium at the location of the first microwave resonator based on the resonance frequency. The method may comprise the steps of generating an electromagnetic signal comprising the resonance frequency of the microwave resonator, transmitting, with the transceiver, the electromagnetic signal along the waveguide. Receiving, with the transceiver, an electromagnetic signal reflected at the microwave resonator, detecting a frequency range of the received electromagnetic signal, having been reflected by the microwave resonator. Determining a density of the content at the location of the microwave resonator based on the determined frequency range, and based on a known relation between the dielectric constant and density of the content.

According to one embodiment of the invention, the method may further comprise correlating a frequency range of said reflected portion of said electromagnetic signal with a resonance frequency range of said microwave resonator between a resonance frequency in air and a resonance frequency in a medium having a known dielectric constant, to verify that said reflected portion of said electromagnetic signal is a result of reflection by said microwave resonator. By correlating the reflected portion with a resonance frequency known under certain conditions an improved identification of the reflection, and an easier correlation to a specific microwave resonator will be provided. Air should in the present context be interpreted broadly. Above the filling level in a tank there is a tank atmosphere which in many cases is similar to air. By being similar, it should be understood that the dielectric constants at different pressures and temperatures will differ only negligibly. Hence, the correlation may often be performed with reference to a resonance frequency in air, and a resonance frequency in a product having a known dielectric constant.

According to another embodiment of the invention, in a system comprising a second microwave resonator having a second resonance frequency, and configured to reflect frequencies corresponding to a second bandwidth around the second resonance frequency, the second bandwidth being smaller than and within the frequency range, the second resonance frequency being separate from the resonance frequency of the first microwave resonator, and depending on a dielectric constant of a medium surrounding the second microwave resonator according to a known relationship. The second microwave resonator is arranged at a location along the waveguide offset from the first microwave resonator, and configured to reflect a portion in the frequency domain corresponding to the second bandwidth when the electromagnetic signal is guided along the waveguide The method may further comprise the steps of generating an electromagnetic signal having a frequency range comprising a resonance frequency for each of the first and the second microwave resonator, and detecting a plurality of reflected portions of a received electromagnetic signal reflected by the first and the second microwave resonator. Determining a density of the medium at each of the known positions of the microwave resonators based on the reflected portions, and based on a known relation between the dielectric constant and density of the medium According to one embodiment of the invention the method may further comprise the step of determining a filling level of a medium in the tank based on a time-of-flight between the transmitted electromagnetic signal and a received electromagnetic signal reflected at a surface of the medium in the tank. Advantageously the method for measuring density is further used also to detect and determine the filling level of the product in the tank, thereby providing a method for measuring both the density and the filling level. Providing a combined measurement method may reduce the costs compared to two separate methods, and further the number of passages needed into the tank may be reduced compared to two separate measurement systems, thus alleviating e.g. customer concerns about long and troublesome installation processes.

According to another embodiment of the invention the method may further comprise the step of determining whether each of the microwave resonators is located above or below a filling level of the product.

The effects, features and advantages of this second aspect of the present invention are largely analogous to those described above in connection with the first aspect of the invention.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

This and other aspects of the present invention will now be described in more detail, with reference to the appended drawings showing embodiments of the invention.

DETAILED DESCRIPTION OF THE PREFERRED EMBODIMENTS

In the present description, embodiments of the present invention are mainly described with reference to a system having a waveguide which is a single-line waveguide such as a Sommerfeld-probe or Goubau-probe. A single-line waveguide typically has a diameter of 4-6 mm and is made of stainless steel. However, any waveguide such as a still pipe, a transmission line, twin-line probe or a coaxial probe may be used in conjunction with the present invention. Further, in the following description, embodiments of the present invention are mainly described with reference to a system capable of determining both density and filling level. Further, it is noted that the electromagnetic signals transmitted from the electronics unit may be generated according to different principles of radar level gauging, i.e. as a Time-Domain Reflectometry sweep (TDR) or as Frequency Modulated Continuous Wave sweep (FMCW) using a stepped or at least sampled FMCW.

Figure 1:
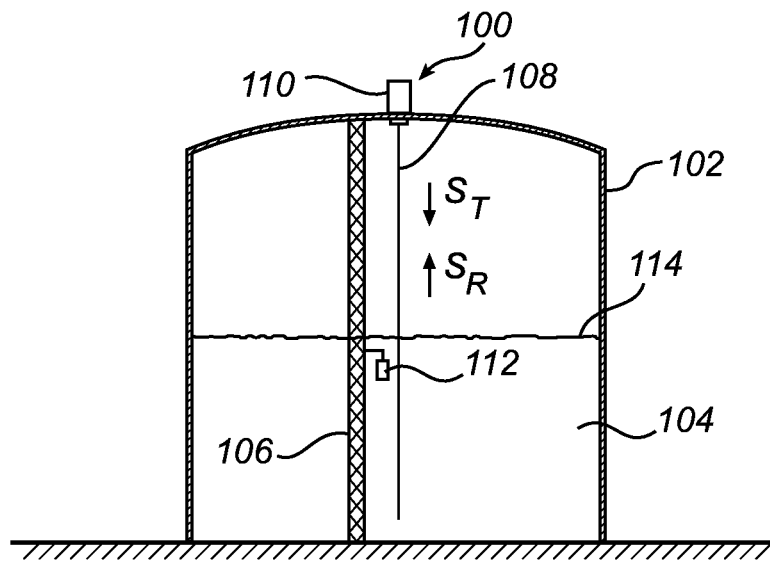
FIG. 1 is a schematic view of a system according to an embodiment of the present invention.

FIG. 1 schematically illustrates a system 100 for determining a density of a non-conducting medium in a tank 102 according to an embodiment of the present invention. The system 100 comprises a measurement electronics unit 110 connected to a waveguide 108. The system 100 is provided on a tank 102, which is partly filled with a product 104 to be gauged, the product 104 being a non-conducting medium. By analyzing a transmitted signal $S_T$ being guided by the waveguide 108 towards the surface 114 of the product 104, and a reflected signal $S_R$ traveling back from the surface 114, the measurement electronics unit 110 can ordinarily determine the distance between a reference position (such as the tank ceiling) and the surface 114 of the product 104, whereby the filling level can be deduced. It should be noted that, although a tank 102 containing a single product 104 is discussed herein, the distance to any material interface along the waveguide can be measured in a similar manner. For example, a FMCW measurement will provide a relatively high measurement sensitivity of the radar level gauge, enabling reliable measurement results also when interfering objects are present in the tank. Furthermore the transmitted signal $S_T$ being guided by the waveguide 108 towards the surface 114, typically has a bandwidth of 2 GHz between 1 to 3 GHz, where for example 1 GHz to 2 GHz may be used for level measurement and 2 GHz to 3 GHz may be used for density measurements. With a small number of microwave resonators the range may be reduced to e.g. 1 GHz to 2.3 GHz. However, it is possible to use the entire bandwidth for both measurements simultaneously.

The system 100 further comprises a microwave resonator 112 arranged along the waveguide 108 on a support structure 106 arranged in the proximity of the waveguide 106 and which support structure 106 extends substantially parallel to the waveguide 106. The microwave resonator 112 has a resonance frequency which has a known relationship to the dielectric constant of a medium surrounding the microwave resonator 112, in this case the product 104 in the tank 102. By a medium surrounding the microwave resonator 112 should be understood that the microwave resonator 112 is immersed in the medium, and the medium thereby also fills the inside of the microwave resonator 112. A signal traveling along the waveguide 108 will have a radial extension which depends on the strength and frequency of the signal. Thus, the microwave resonator 112 is arranged at a distance from the waveguide 108 and is e.g. capacitively or inductively coupled to the waveguide 108 in order to be able to reflect a portion of the signal corresponding to the resonance frequency of the microwave resonator 112. The microwave resonator 112 will resonate at the corresponding resonance frequency and reflect a portion in the frequency domain of an electromagnetic signal traveling along the waveguide 108. The reflected portion of the electromagnetic signal will be detected by the measurement electronics unit 110, thus indicating the resonance frequency of the microwave resonator 112. By knowing the relationship between the resonance frequency and the dielectric constant, the dielectric constant is may be determined from the resonance frequency. Thus, by knowing the relationship between the dielectric constant and density, the density at the location of the microwave resonator 112 is determined by the measurement electronics unit 110. These known relationships are further described and discussed later. The transmitted signal $S_T$ may be used to combine level measurement with a density measurement, or the transmitted signals may be used alternating for density measurements and level measurement in order to efficiently measure them separately. Likewise the hardware comprised in the measurement electronics unit 110 which provides the signal and determines the density and/or level may be the same or separate units for the two measurements. As mentioned earlier the density and level measurement may also be separated in frequency, i.e. the measurements are performed in different frequency ranges.

Figure 2:
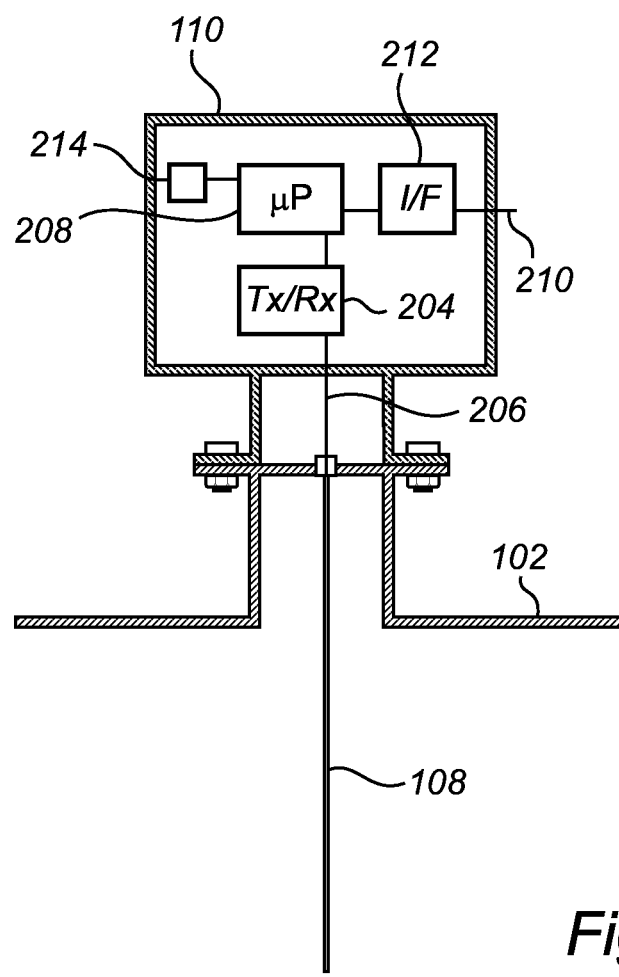
FIG. 2 is a detailed view of the measurement electronics unit comprised in the system of FIG. 1.

As is illustrated in FIG. 2, the measurement electronics unit 110 comprises a transceiver 204 configured to generate, transmit and receive electromagnetic signals in the microwave range, which is connected to the waveguide 108 via a connection line 206. It is noted that the waveguide 108 optionally may be connected directly to the transceiver 204, or be connected via a suitable signal connection, such as a coaxial cable. The measurement unit 110 further comprises processing circuitry 208, which is connected to the transceiver 204 for control of the transceiver 204 and processing of a signal received by the transceiver 204 to determine e.g. the density at the location of the microwave resonator 112 and/or the filling level of the product 104 in the tank 102. The processing circuitry 208 is also connected to a memory 214, storing any software required for the operation of the system 100, and also providing RAM used during operation.

The processing circuitry 208 is further connectable to external communication lines 210 for analog and/or digital communication via an interface 212. As an example, the communication between the communication interface 212 and an external control station (not shown) can be provided by a two-wire interface, which has a combined function of both transmitting the measurement result to the control station and receiving power for operation of the system 100. Such a two-wire interface may provide a more or less constant power, and the measurement result can be superimposed on the power voltage using a digital protocol, such as Fieldbus Foundation, HART or Profibus. Alternatively, the current in the lines is regulated in accordance with the prevailing measurement result. An example of such an interface is the 4-20 mA industrial loop, where the current is regulated between 4 and 20 mA, depending on the measurement result. Alternatively, the system 100 may communicate wirelessly with the control station using e.g. a Wireless HART protocol, and use a local power supply (not shown) with batteries or means of scavenging energy for autonomous operation.

The interface 212 here includes power management circuitry, including a power storage (not shown) for storing power during periods when the microwave unit is inactive, thereby enabling higher power consumption during periods when the transceiver 204 is active (i.e. during measurement). With such power management, lower average power consumption may be achieved, while still allowing short periods of higher power consumption. The power storage (not shown) may include a capacitor, and may be restricted by space requirements as well as intrinsic safety requirements (applying when the system 100 is arranged in the hazardous zone of a tank with explosive or flammable contents)

Although being shown as separate blocks in FIG. 2, several of the transceiver 204, the processing circuitry 208, memory and the interface 212 may be provided on the same circuit board, or even in the same circuit.

While the elements of the transceiver 204 are typically implemented in hardware, and form part of an integrated unit normally referred to as a microwave unit, at least some portions of the processing circuitry 208 are typically embodied by software modules executed by an embedded processor. The invention is not restricted to this particular realization, and any implementation found suitable to realize the herein described functionality may be contemplated.

Referring now to FIG. 3A to 3E there is shown five embodiments of microwave resonators 300, 310, 320, 340, 360 which are suitable for use in the present invention. It should be noted that the microwave resonators 300, 310, 320, 340, 360 merely represent a non-exhaustive number of embodiments, other embodiments or variants of the shown embodiments suitable for the present invention can be contemplated by the person skilled in the art based on the shown examples.

Figure 3A:
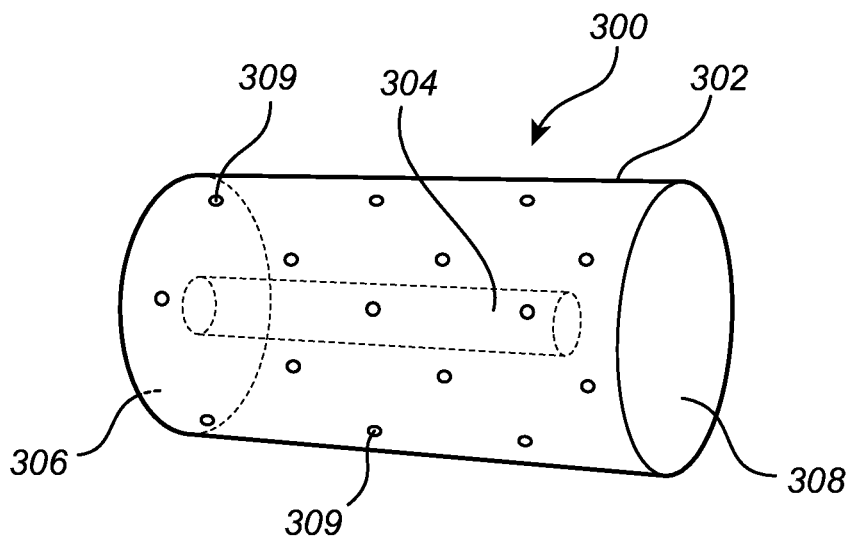
FIGS. 3A to 3E are schematic views of embodiments of microwave resonators suitable for implementing the present invention.

In FIG. 3A a horizontally aligned microwave resonator 300 having a longitudinal axis of extension is shown, preferably having a small tilt towards the opening so that a material (liquid) does not remain in the microwave resonator 300. The microwave resonator 300 in FIG. 3a comprises a housing 302 having a tubular shape i.e. a circular cylindrical shape, there is an open end 308 of the tubular housing and a closed end 306. To further ease the draining, and filling of a liquid in the microwave resonator 300 holes 309 are provided on the housing 302, the holes 309 are small, preferably having a diameter less than 4 mm. The suitable diameter for a given application is determined by the diameter of the resonator and by the resonance frequency. The hole should be sufficiently small such that it does not influence the properties of the resonator, and it should be smaller than the wavelength of the resonance frequency. Furthermore, the microwave resonator 300 comprises an inner rod 304 which is fixed to the closed end 306 and extends from the closed end 306 towards the open end 308 within the tubular housing 302. In use, the inner rod 304 will act as a receiving antenna, thus the length of the inner rod 304 and the dielectric constant of the medium surrounding and filling the microwave resonator 300, 310 determines the resonance frequency of the microwave resonator 300, 310. The open end 306 will capacitively couple an electromagnetic signal in the microwave range having energy distributed over a range of frequencies to the inner rod 304. The housing 302 will extend further than the inner rod 304, thus ensuring that the inner rod 304 is substantially non-radiating, i.e. that it does not form a radiating antenna. One suitable length of the inner rod 304 is 15-40 mm, and the housing 302 then has a typical length which is 10 mm longer. A shorter inner rod 304 provides a higher resonance frequency and a longer inner rod 304 provides a lower resonance frequency. Furthermore, the diameter of the housing 302 will determine how large the bandwidth i.e. how far the range extends around the resonance frequency where the microwave resonator 300, 310 may reflect substantial portions of the electromagnetic signals traveling along the waveguide. A typical inner diameter of the housing 302 of 10-25 mm will correspond to a bandwidth of approximately 1 MHz around the resonance frequency, a smaller diameter will provide a smaller bandwidth and vice versa. The inner rod 304 will have a diameter which is about 30 to 40 percent of the inner diameter of the housing 302, and for the range given above, the diameter will thus be approximately 5 mm. Note that it is the open end 308 of the microwave resonator 302 which will capacitively couple a signal from the waveguide 108 comprising the resonance frequency and frequencies in the bandwidth around the resonance frequency to the microwave resonator. Hence, the microwave resonator 302 will in the typical case be oriented with the open end 308 towards the waveguide 108, at a distance of 5-10 mm from the waveguide 108 and thus a non-conducting medium between the microwave resonator 302 and the inner rod 304 will act as a capacitive element (i.e. a capacitor). The size of this capacitance will thus be decided by both the distance and the dielectric constant of the non-conducting medium between the resonator 302 and waveguide 108. A suitable resulting capacitance may be approximately 0.01 pF to 1 pF.

Figure 3B:
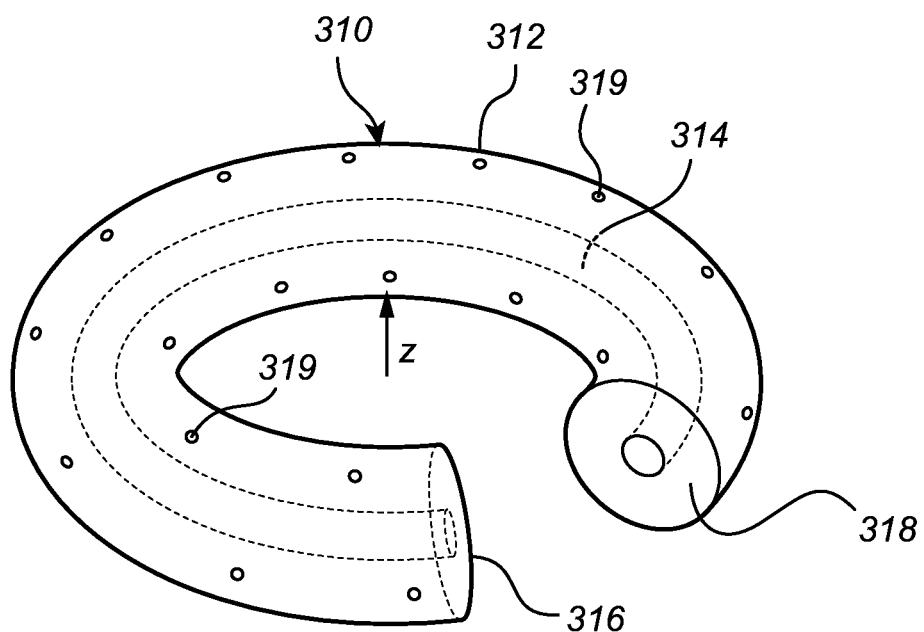

FIG. 3B shows another embodiment of a microwave resonator 310 according to the principle described above. The microwave resonator 310 comprises a housing 312 having a tubular shape, compared to the earlier embodiment the housing 312 has an annular shape as a non-completed torus. The housing 312 further comprises a closed end 316 and an open end 318. Furthermore, the microwave resonator 310 comprises an inner rod 314 which is fixed to the closed end 316 and extends from the closed end 316 towards the open end 318 within the tubular housing 312. The function of the microwave resonator 310 is essentially the same as the above described microwave resonator 312, i.e. the correspondence to frequency is the same. The difference is the annulus-shape forming a non-complete torus thus enabling alternative positions, locations or arrangements for the microwave resonator 310.

Figure 3C:
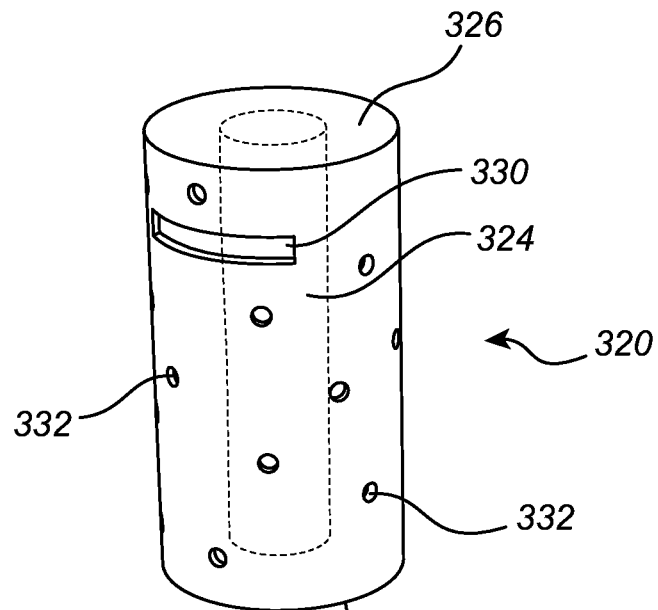

FIG. 3C shows an embodiment of a microwave resonator 320, which differs from the resonators 300 and 310 by being inductively coupled to the waveguide 108. The microwave resonator 320 is vertically arranged, and has a housing 328 having a tubular shape i.e. a circular cylindrical shape, there is an open end of the tubular housing which is positioned at the lower end, and a closed end 326 positioned upwards of the open end. To further ease the draining and filling of a liquid in the microwave resonator 320, holes 332 are provided on the housing 302. The holes 332 are relatively small, preferably having a diameter less than 4 mm. The small diameter will allow them to have a negligible influence on the measurement simultaneously as being beneficial to the draining and filling of the microwave resonator 320. Furthermore, the resonator 320 comprises an inner rod 324 which is fixed to the closed end 326 and extends from the closed end 326 towards the open end within the tubular housing 328. In use, the inner rod 324 will act as a receiving antenna, and the dimension and functions of the components of the microwave resonator 320 are similar to the functionality of the microwave resonators 300, 310 described above. The main difference of the microwave resonator 320 is the inductive coupling which is enabled by providing a an opening in a sidewall of the housing 328, here in the form of a slit 330. Thus by arranging the microwave resonator 320 vertically, in proximity to a waveguide 108, signals comprising the resonance frequency or frequencies within the bandwidth around the resonance frequency may be inductively coupled from the waveguide 108, which is parallel to the inner rod 324. Hence, whereas the resonance frequency and bandwidth depends on the same factors as for the capacitively coupled microwave resonators 300, 310, the strength of the inductive coupling will depend mainly on the size of the slit 330 i.e. the window through which the inner rod 324 may couple electromagnetically to the waveguide 108, and on the distance between the inner rod 324 and the waveguide 108. The size of the slit 330 may be controlled for instance by increasing how far around the circumference the slit 330 runs, or the height e.g. the distance along the vertical longitudinal axis the slit 330 opens.

Figure 3D:
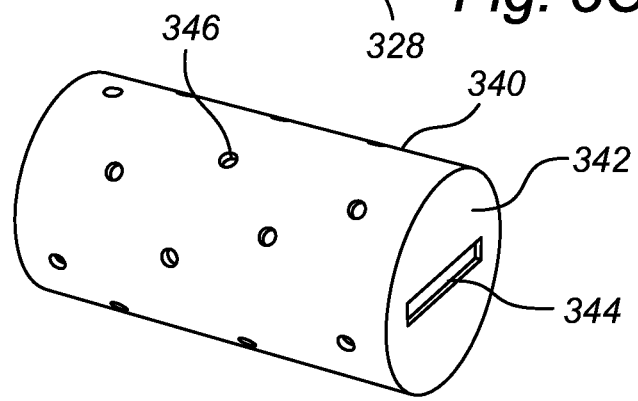

FIG. 3D shows a microwave resonator, here in the form of a cylindrical circular container 340. The container comprises end plates 342 in which there is an opening, here in the form of a slit 344. In order for a medium in which the container 344 is immersed to fill the container, the container 340 further comprises holes 346. The holes 346 have similar dimensions and functionality as the holes 309 discussed earlier, e.g. the holes 346 help with the draining and filling of the container 340 and they are much smaller than the wavelength of the resonance frequency of the container 340. The slit 344 will enable the container 340 to be arranged at a distance from a waveguide 108 with the slit 344 facing the waveguide 108 and inductively couple the signal being guided along the waveguide to the container 340. To provide a resonance frequency in the order of 2 GHz the container 340 will be approximately at least 8 cm long and have a diameter of approximately at least 8 cm as well. A container 340 having a length and diameter of about 13 cm will for example provide a high Q-value for the $TE_{011}$-mode.

Figure 3E:
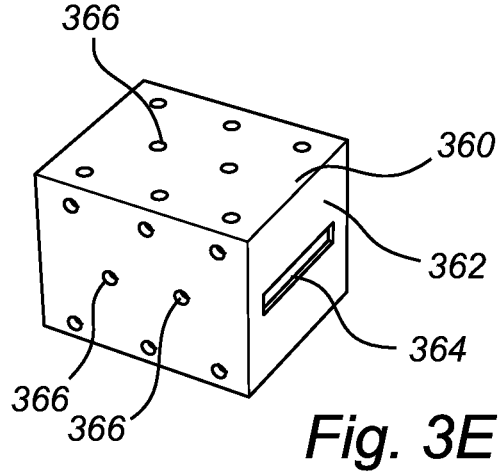

FIG. 3E shows a microwave resonator, here in the form a rectangular container 360. The container comprises an endplate 362 in which there is an opening, here in the form of a slit 364. In same way, as for the container 340 with respect to dimensions and functionality, the container 360 also comprises holes 366. The slit 364, in use, will face the waveguide 108 at a distance, and inductively couple the signal being guided along the waveguide into the container 360. To provide a resonance frequency in the order of 2 GHz the container 360 can be made approximately at least 4 cm long, 7 cm wide and 7 cm high. The length is defined along the axis running through the endplates. However, It is also possible to use other types of electromagnetic resonators known by the skilled person.

Figure 4:
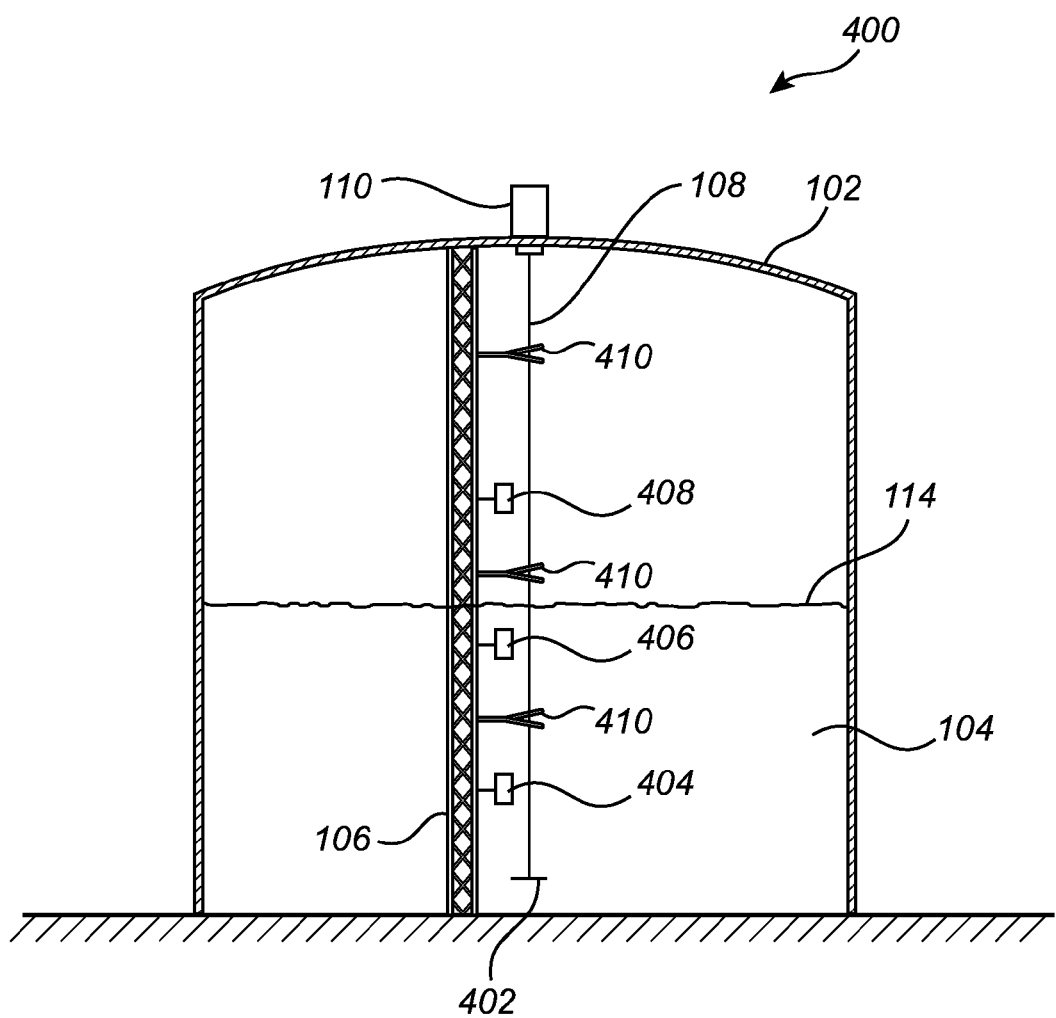
FIG. 4 is a schematic view of a system suitable for implementing an embodiment the present invention.

FIG. 4 shows another embodiment of the present invention, where a measurement electronics unit 110 is mounted on top of a tank 102. The tank contains a product 104 having a surface 114, measurements may be performed to e.g. provide the density and/or filling level and thus provide the operator or owner with information of the amount of product 104 within the tank 102. The system 400 comprises a waveguide 108, the waveguide 108 shown in FIG. 4 further comprises an end-of-waveguide element 402. The waveguide 108 preferably extends as far into the tank as required to measure a desired filling level. Therefore, a waveguide 108 may extend and be mechanically connected i.e. attached to the bottom of the tank 102 for mechanical stability and ability to measure filling level all the way to the bottom of the tank 102. Alternatively, for example as indicated by the end-of-probe element 402 the waveguide 108 is not securely attached to the bottom, and the end-of-probe element 402 may instead be a weight to stabilize the probe 108.

The system 400 also comprises a support structure 106. On the support structure, three microwave resonators 404, 406, 408 are arranged at different heights along the waveguide 108. The first microwave resonator 404 is located the furthest from the measurement electronics unit 110, the second microwave resonator 406 is located in between the first and third microwave resonator 408, the third microwave resonator 408 being located closest to the measurement electronics unit 110. Further, in FIG. 4 both the first and the second microwave resonators 404, 406 are located below the surface 114 while the third microwave resonator 408 is located above the surface 114. The support structure 106 further comprises retaining elements 410 for ensuring that the waveguide 108 and the microwave resonators 404, 406, 408 are separated by at least a predetermined distance and a maximum distance decided by the design of the retaining elements. Each of the three microwave resonators 404, 406, 408 shown in FIG. 4 has a resonance frequency range which does not overlap with the resonance frequency of any of the other microwave resonators at any expected dielectric constant for the product 104 to be measured or the environment in the tank.

Figure 5A:
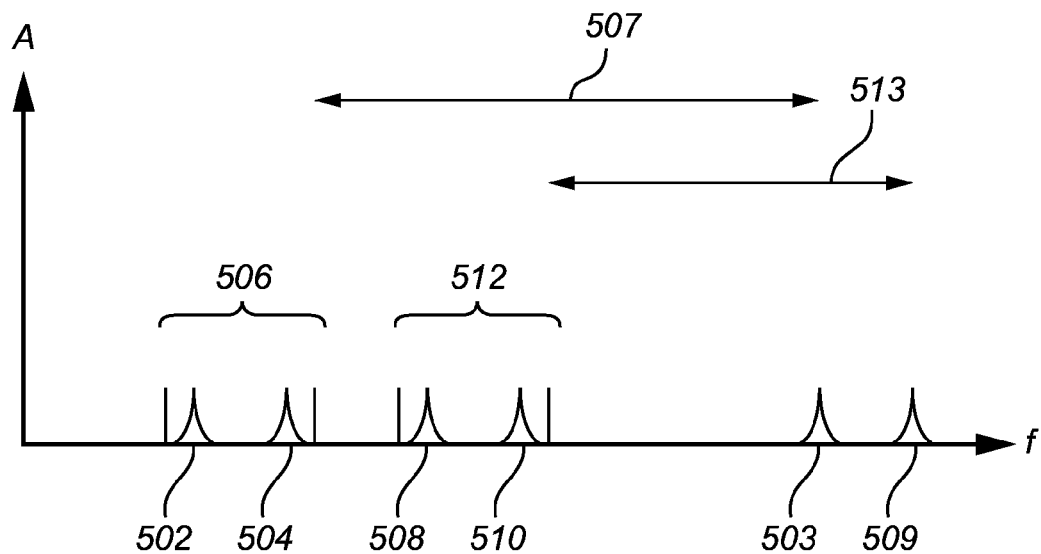
FIG. 5A schematically illustrates the reflection from two microwave resonators.

In FIG. 5a there is shown a graph comprising a schematic plot of frequency on the horizontal axis and amplitude on the vertical axis. An example response for two microwave resonators as described for example in FIGS. 3A and 3C is shown as the indicated peaks 502, 503, 504, 508, 509, 510. The peaks 502, 503, 504, 508, 509, 510 have a Gaussian distribution to indicate that there is a range, i.e. a bandwidth, around the resonance frequency of about 1 MHz or less where the microwave resonator reflects portions of electromagnetic signals comprising the frequencies within the bandwidths.

Furthermore, the range of resonance frequencies for the two microwave resonators under typical operating conditions that correspond to the expected values of the dielectric constant for the medium surrounding the microwave resonators are indicated by the ranges 506 and 512. Thus, the highest frequency for the first resonator corresponding to the peak 504 within the range 506 would typically be achieved when the microwave resonator is immersed just below the surface 114 of a product to be measured. The lowest frequency for the first resonator will correspond to the peak 502 within the range 506, and would typically be achieved if the tank 102 is full and the resonator is located at the bottom of the tank 102 at the point with the highest pressure, and thus density of the medium. The same principle applies for the lowest frequency for the second resonator at the peak 508 and the highest frequency at the peak 510 which are both within the range 512.

If the resonators are located above the surface 114 of the product, they will have resonance frequencies which are higher than, and outside of the ranges 506, 512. To illustrate this, the first resonator will above the surface be surrounded by a tank atmosphere with a dielectric constant close to one, and will have a high resonance frequency represented by the peak 503. When immersed in a medium, the resonance frequency will accordingly have a resonance frequency within the range 506. The arrow 507 represents the distance between the peak 503 and the range 506. By the same principle the second microwave resonator will above the surface have a resonance frequency corresponding to the peak 509 which will decrease to be within the range 512 as soon as it is immersed in a medium The arrow 513 represents the distance between the peak 509 and the range 512.

Note that the resonance frequency ranges 506, 512 are separated and thus do not overlap at any expected dielectric constant i.e. density of the product to be measured. Thus the density will be measurable at the locations of each microwave resonator, and further the microwave resonators do not interfere with each other. By not interfering with each other it should be understood that there is no possibility for an reflected portion of a signal to be misinterpreted as belonging to the first microwave resonator when in fact it belongs to the second microwave resonator and vice versa.

Figure 5B:
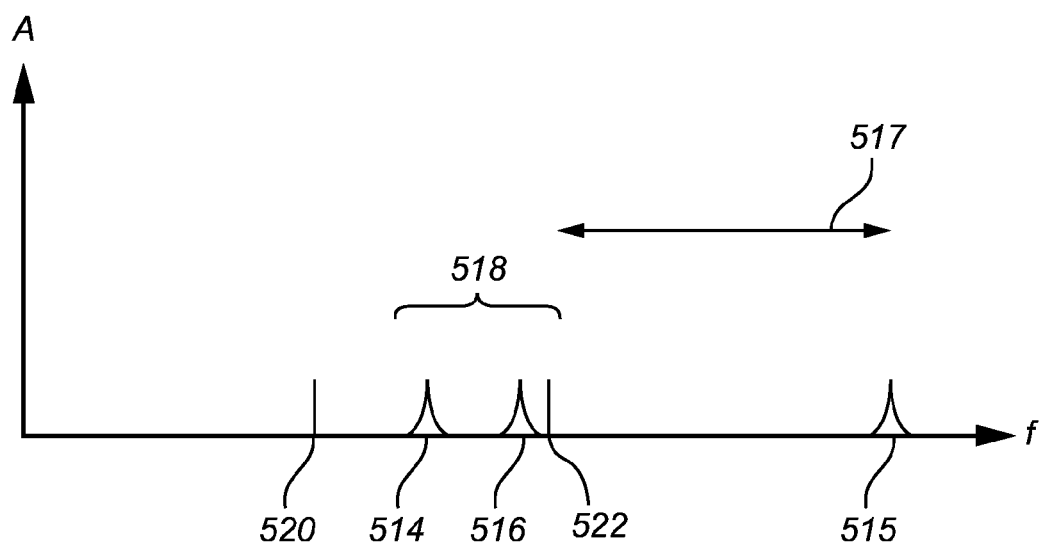
FIG. 5B schematically illustrates the reflection from a microwave resonator.

To further elucidate the principle, a situation where the surface 114 rises from below to above a microwave resonator, for example when an empty tank is being filled, may essentially be illustrated by FIG. 5b. First, an exemplary microwave resonator is above the surface 114 and thus filled with tank atmosphere having a dielectric constant close to one and thus exhibiting a resonance frequency illustrated by the peak 515. Then, the surface rises 114 as the tank is being filled with a product 104. Secondly, at a certain point in time during filling, the surface 114 will reach above the microwave resonator and the microwave resonator will be immersed in the product. The resonance frequency of the microwave resonator will then shift down to within a resonance frequency range indicated by the boundaries indicating the lowest resonance frequency 520 and the highest resonance frequency 522 for the product. A typical product for the present invention such as LNG and LPG will most generally have a higher dielectric constant at a higher density. A higher density is usually found further down in a tank where the pressure is higher. However stratification as mentioned earlier may occur. Thus as the filling action continues, the resonance frequency should go from a high value within the resonance frequency range as indicated by the peak 516 towards a lower resonance frequency indicated by the peak 514. The distance 518 illustrates the shift in resonance frequency corresponding to the change in density. Note that peak 514 does not correspond to the lowest possible resonance frequency within the resonance frequency range. Thus, further filling or pressurization of the tank may further decrease the resonance frequency.

As an example, immersed resonators may have resonance frequencies within 2.1 GHz to 2.7 GHz, where each resonator has a resonance frequency range of 0.04 GHz and the resonance frequency ranges of the microwave resonators are separated from each other by 0.05 to 0.1 GHz. The above would provide microwave resonators having resonance frequencies higher than 3 GHz when they are above the surface i.e. filled by tank atmosphere. Hence, filling level measurement may be performed at 1-2 GHz, density measurement of a product in the tank may be performed at 2-3 GHz, and the system may also determine if the microwave resonators are empty by transmitting a signal above 3 GHz. Thus, the density measurement and filling level measurement may be separated. However, it is also possible to decrease the resonance frequencies of the microwave resonators to measure density at 1-2 GHz.

Figure 6A:
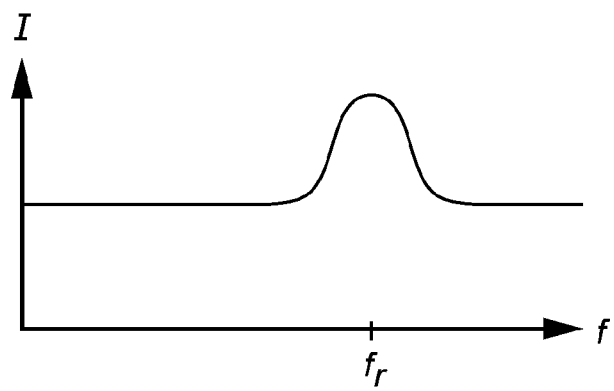
FIG. 6A schematically illustrates a received reflected electromagnetic signal according to various embodiments of the present invention.

In FIG. 6A there is shown a schematic plot of intensity against frequency for a received electromagnetic signal comprising a range of frequencies which comprises all possible resonance frequencies for a given configuration. Note the reflection at the resonance frequency $f_r$ corresponding to a microwave resonator having reflected a portion of the signal at the resonance frequency and a bandwidth i.e. range around the resonance frequency. Hence, a peak in the intensity of the signal can be seen at and around the resonance frequency since a microwave resonator will reflect a portion of the signal.

Figure 6B:
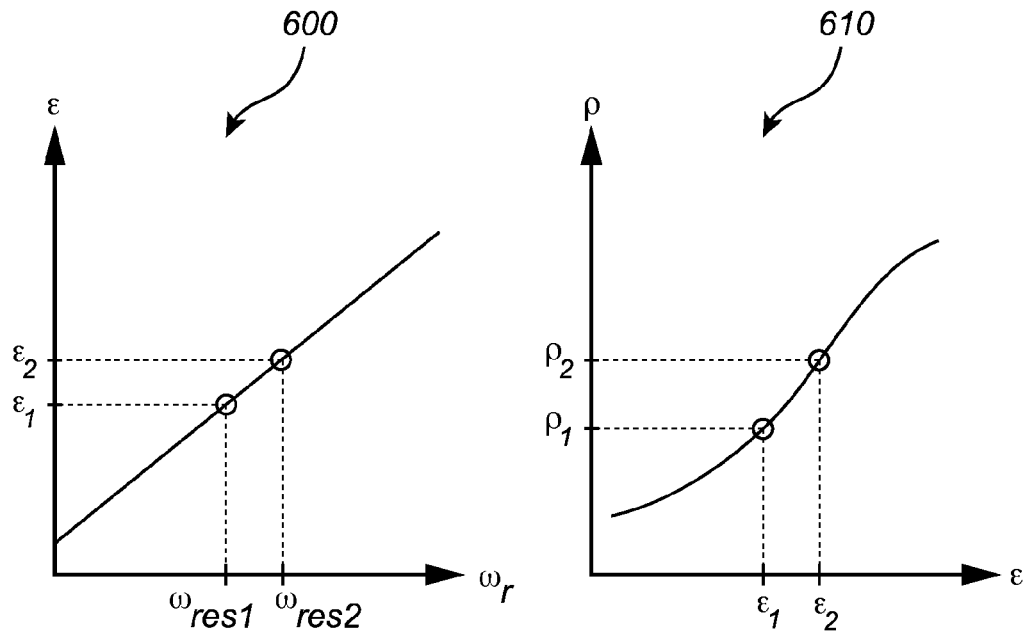
FIG. 6B shows an example of a known relationship between the density, dielectric constant and resonance frequency.

FIG. 6B schematically shows a first graph 600 illustrating resonance frequency versus dielectric constant for a microwave resonator, and also a second graph 610 showing the relationship between dielectric constant and density for a non-conducting medium. As shown in the first plot 600 the relationship between the resonance frequency and the dielectric constant is known from construction, design and/or theoretical calculations of the microwave resonator, thus a first resonance frequency $\omega_{res1}$ corresponds to a first dielectric constant $\in_1$ according to the known relationship between a resonance frequency and a dielectric constant, and a second resonance frequency $\omega_{res2}$ will correspond to a second dielectric constant $\in_2$. Further, the first dielectric constant $\in_1$ will then correspond to a first density $\rho_1$ of the medium according to the known relationship for the dielectric constant and density shown in the second plot 610, and the second dielectric constant will correspond to a second density $\rho_2$ of the medium. The relationship between the dielectric constant and the density of the medium may be described by a function, or it may be known as discrete values in a look-up-table made by empirical studies, in any case the transition from determining a resonance frequency to determining the density is understood through the described connection in FIG. 6B. It should be noted that the plotted curves in the plots are merely for illustrative purposes, therein shown as mostly linear. However, the relationship between the dielectric constant and resonance frequency may be different for different materials, such as the resonance frequency being inversely proportional to the square root of the dielectric constant. The general principle thus applies to any relationship and is not limited to the one shown. To provide an example, the resonance frequency will vary as the inverse square root of the dielectric constant for the microwave resonator shown in FIG. 3A. Therefore, assuming a medium having a dielectric constant of 2, the resonance frequency of the microwave resonator will differ about 30 percent when immersed in the medium compared to when above the surface.

Figure 7:
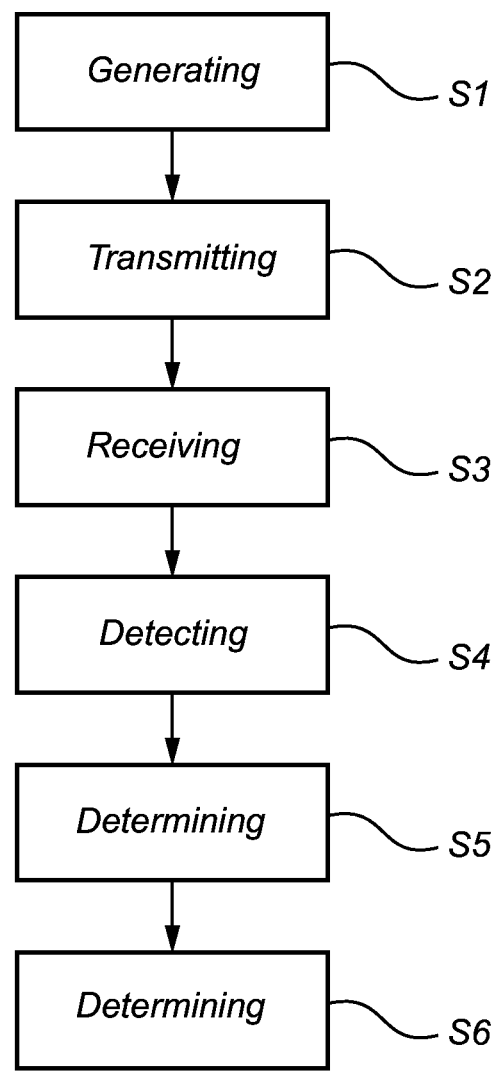
FIG. 7 is a flow chart outlining the general steps of a method according to the present invention.

In FIG. 7, a flowchart showing the general steps of a method for determining the density according to the invention is shown. First in step S1 an electromagnetic signal in the microwave range is generated in the transceiver 204, the generated signal having energy distributed over a range of frequencies. The generated signal further comprises the resonance frequencies of the microwave resonator 112 or resonators 404, 406, 408 comprised in the system.

Secondly, in step S2, the electromagnetic signal is transmitted from said transceiver 204 along the waveguide 108 towards the surface 114 of the product kept in the tank 102. In step S3 an electromagnetic signal resulting from the reflection of the transmitted electromagnetic signal by a microwave resonator 112 is received by the transceiver 204.

Then in step S4, the processing circuitry 208 connected to the transceiver 204 detects a portion of the received electromagnetic signal which been reflected by at least one microwave resonator 112. The reflected portion of the signal corresponds to a frequency, which is the resonance frequency of the microwave resonator 112 at the moment of reflection.

In step S5 the density of the medium, i.e. product if the surface 114 is above the microwave resonator 112, at the location of the microwave resonator 112 based on the reflected portion indicating a resonance frequency of the microwave resonator 112, which thus indicates the dielectric constant of the surrounding medium is determined. The determination of the density is based on a known relation between the dielectric constant and density of the product.

Then, optionally, in step S6 a filling level of the product kept in the tank may be determined from ordinary time-of flight techniques such as FMCW or TDR which are not further elaborated on herein but are well known to the person skilled in the art.

The method may for example also comprise correlating the reflected portion of the received electromagnetic signal with a resonance frequency known under certain conditions of the microwave resonator 112, to verify that the reflected portion of the signal is a result of reflection by the microwave resonator 112. A resonance frequency known under certain conditions may for example be a measurement done after installation of the system when the tank is empty and filled by an ordinary tank atmosphere, the tank atmosphere will then be surrounding the microwave resonator 112. Hence a measurement of the resonance frequency of the microwave resonator 112 surrounded by a medium having a dielectric constant very close to one (the dielectric constant for air is 1.0006 at standard temperature and pressure, STP, and the dielectric constant for e.g. methane is 1.0008 at STP) is provided and may be used for correlating the reflected portion of the signal to each microwave resonator 112 comprised in the system 400, 100. Furthermore, the predetermined distance from the microwave resonator 112 to the waveguide 108 may also be tuned directly after installation of the system. A signal would then be generated and sent along the waveguide and the resonance frequencies would be detected according to the just described correlation, however the amount of reflection will be dependent on the distance of the microwave resonator 112 to the waveguide 108 thus a microwave resonator arranged too far away from the waveguide 108 will not reflect enough of the signal and while a microwave resonator 112 arranged close to the waveguide 108 will reflect a sufficient portion of the signal. However, a microwave resonator 112 arranged too close to the waveguide 108 will absorb too much of the signal, and the bandwidth around the resonance frequency will also become larger. Therefore, for a microwave resonator 112 arranged too close to the waveguide 108 it becomes harder to both distinguish the reflection from the microwave resonator 112 compared to the reflection from an impedance transition such as a surface of a medium in the tank, and too determine the resonance frequency from the received portion of the signal which has been reflected by the microwave resonator 112 as the bandwidth larger. Thus by performing a test after installation the predetermined distance between the waveguide 108 and microwave resonator 112 may be tuned in order to optimize the system. It should be noted that the proper distance will be dependent on a large number of factors such as the type and size of the waveguide used, the product, the strength of the signal and more, thus a manual tuning of the distance may be one simple way to tune the system.

Referring now to FIG. 8A to 8D there is shown examples of how to attach or arrange a microwave resonator in proximity of a waveguide 108.

Figure 8A:
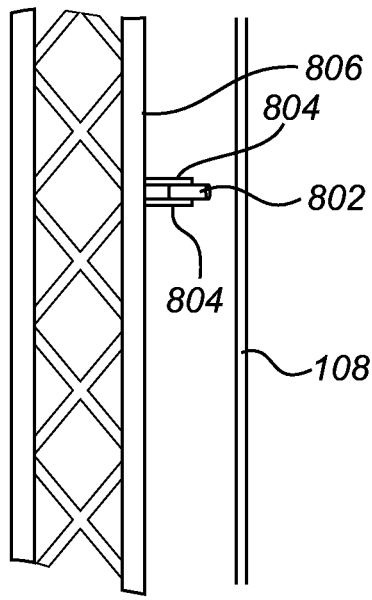
FIGS. 8A to 8D are schematic views of embodiments on attachments or arrangements between the waveguide and microwave resonators.

In FIG. 8A, a capacitively coupled resonator 802 is arranged in close proximity of the waveguide 108. There is a support structure, here shown as generic metal scaffolding 806. On the scaffolding 806 there are two holding elements 804 formed by two plates of PTFE about 1 to 2 mm thick. The resonator 802 is held between the two plates 804 in order to arrange it at a predetermined distance from the waveguide. The predetermined distance may for example be 10 mm or less to provide a suitable capacitive coupling between the open end of the resonator 802 and the waveguide 108.

Figure 8B:
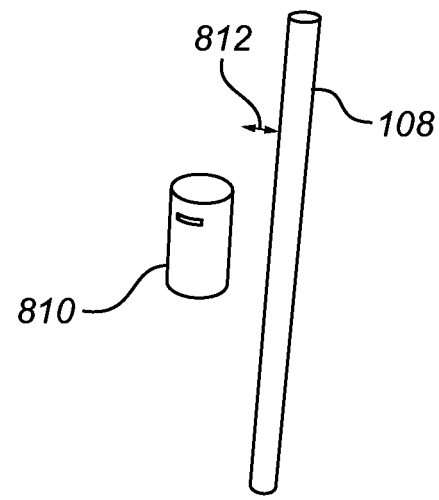

In FIG. 8B, conversely to FIG. 8A there is an inductively coupled resonator 810 arranged at a distance 812 from the waveguide. A signal being guided along the waveguide 108 will inductively couple to the inner rod of the resonator 810 as described above through the slit. The distance 812 and the size of the slit will determine the strength of the coupling, a distance of 10 mm or less or even lower as 5 mm or less may be suitable when the resonator 810 is arranged at a distance. Although not shown explicitly, scaffolding and plates of PTFE may for example be used to keep the distance 812 between the resonator 810 and the waveguide 108.

Figure 8C:
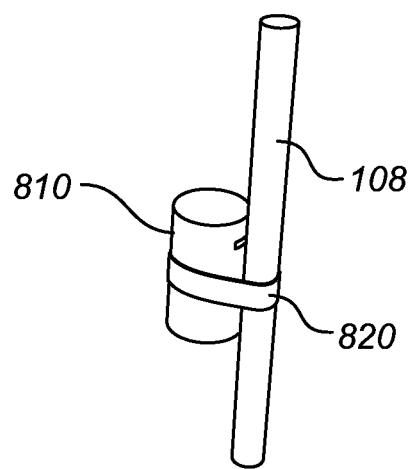
Figure 8D:
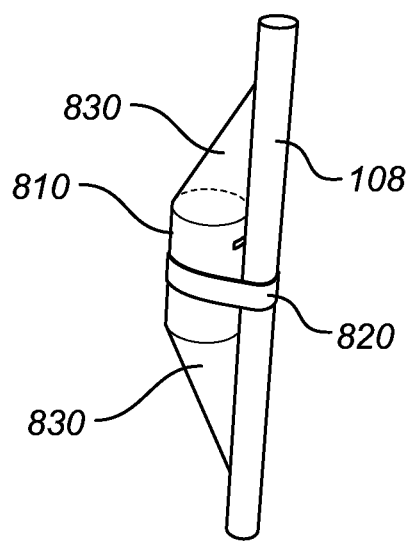

For the inductively coupled resonator 810 which has its longitudinal axis parallel with the waveguide there is also the possibility to directly attach it to the waveguide as shown in FIG. 8C. A clamping element, here shown as a band 820 may be used. The band may be made of metal or plastic or any other suitable material which is capable of withstanding the low temperatures used in connection with LPG or LNG. The slit size may then be made smaller in order to tune the strength of the coupling when the inner rod will be closer to the waveguide 108. A resonator 810 attached directly to the waveguide 108 as in FIG. 8C may cause an unwanted broadband reflection (e.g. a reflection at all frequencies). Therefore, in FIG. 8D there is a microwave resonator 810 arranged as in FIG. 8C, however the arrangement now further comprises a step, or ramp in size, here shown as a cone 830. The cones 830, which are preferably made of metal will decrease the broadband reflection caused by attaching the resonator 810 directly to the waveguide 108. The decrease in broadband reflection is due to the ramping or stepping of the apparent thickness of the waveguide 108 causing small impedance transition, instead of an abrupt increase in thickness which will give rise to an abrupt increase in impedance and thus a broadband reflection of the signal being guided along the waveguide 108.

Although the figures may show a specific order of method steps, the order of the steps may differ from what is depicted. Also two or more steps may be performed concurrently or with partial concurrence. Such variation will depend on the software and hardware chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the invention has been described with reference to specific exemplifying embodiments thereof, many different alterations, modifications and the like will become apparent for those skilled in the art. For example, the resonators shown in FIG. 3D and FIG. 3E are not shown attached or arranged in the proximity of the probe. However, the skilled addressee and person skilled in the art will easily understand that these resonators may also be arranged according to the examples given for arranging a microwave resonator along the waveguide. Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

What is claimed is:

1. A system for determining a density of a non-conducting medium in a tank, wherein a relationship between a dielectric constant and a density of said medium is known, and wherein the density is mass per unit volume, said system comprising:
    a transceiver configured to generate, transmit and receive a microwave electromagnetic signal comprising frequencies within a predetermined frequency range;
    a waveguide connected to said transceiver and extending towards and into said medium, arranged to guide a transmitted electromagnetic signal towards and into said medium inside said tank, and to return an electromagnetic signal resulting from a reflection of said transmitted electromagnetic signal;
    a first microwave resonator having a resonance frequency, and configured to reflect frequencies corresponding to a first bandwidth around said resonance frequency, said first bandwidth being smaller than and within said frequency range, said resonance frequency depending on a dielectric constant of a medium surrounding said resonator according to a known relationship;
    wherein said first microwave resonator is arranged at a location along said waveguide, and configured to reflect a portion of an electromagnetic signal, in the frequency domain, corresponding to said first bandwidth, when said electromagnetic signal is guided along said waveguide; and
    processing circuitry connected to said transceiver and configured to:
    determine said resonance frequency based on a reflected portion of a received signal having been reflected by the first microwave resonator, said processing circuitry being further configured to:
    determine a density of said medium at the location of said first microwave resonator based on said resonance frequency.

2. The system according to claim 1, wherein said frequency range is at least two times greater than said first bandwidth.

3. The system according to claim 1, wherein said first bandwidth is approximately 1 MHZ or less.

4. The system according to claim 1, wherein said medium is a low viscosity liquid.

5. The system according to claim 1, wherein said microwave resonator is configured to have a higher resonance frequency at a lower dielectric constant of said medium surrounding said microwave resonator.

6. The system according to claim 1, wherein said microwave resonator is arranged at a distance from said waveguide such that a portion of said signal propagating along said waveguide is reflected when reaching a location of said resonator.

7. The system according to claim 6, wherein said microwave resonator is capacitively coupled to said waveguide.

8. The system according to claim 6, wherein said microwave resonator is inductively coupled to said waveguide.

9. The system according to claim 1, further comprising:
    a support structure arranged in the proximity of said waveguide and extending substantially in parallel with said waveguide, wherein said microwave resonator is arranged on said support structure.

10. The system according to claim 9, further comprising a plurality of retaining elements arranged at fixed positions in relation to an inside of said tank and spaced apart along said waveguide, wherein each of said plurality of retaining elements is arranged to maintain a predetermined minimum distance between said waveguide and said microwave resonator.

11. The system according to claim 10, wherein at least one of said plurality of retaining elements is attached to said support structure.

12. The system according to claim 1, wherein said microwave resonator comprises: a tubular housing having an open end, a closed end and an inner rod fixedly attached to said closed end, and extending along a central axis of said housing from said closed end towards said open end.

13. The system according to claim 11, wherein said inner rod has a length in the range of 15 to 40 mm.

14. The system according to claim 11, wherein said tubular housing is longer than said inner rod, such that said inner rod does not extend out of said open end of said tubular housing.

15. The system according to claim 14, wherein said tubular housing has an inner diameter in the range of 10 to 25 mm.

16. The system according to claim 11, wherein said microwave resonator is substantially horizontally aligned.

17. The system according to claim 11, wherein said microwave resonator is substantially vertically aligned having said open end arranged pointing in a downward direction.

18. The system according to claim 1, further comprising filling level determination circuitry configured to determine a filling level of a product in said tank based on a time-of-flight between said transmitted signal and a received reflected electromagnetic signal reflected at a surface of said medium in said tank.

19. The system according to claim 1, further comprising:
a second microwave resonator having a second resonance frequency, and configured to reflect frequencies corresponding to a second bandwidth around said second resonance frequency, said second bandwidth being smaller than and within said frequency range, said second resonance frequency being separate from the resonance frequency of said first microwave resonator, and depending on a dielectric constant of a medium surrounding said second microwave resonator according to a known relationship;
wherein said second microwave resonator is arranged at a location along said waveguide offset from said first microwave resonator, and configured to reflect a portion of an electromagnetic signal, in the frequency domain, corresponding to said second bandwidth, when said electromagnetic signal is guided along said waveguide; and
said processing circuitry is further configured to determine said second resonance frequency based on a reflected portion of a received signal having been reflected by said second microwave resonator, and determine a density of said medium at the location of said second microwave resonator based on said second resonance frequency.

20. The system according to claim 19, wherein said first microwave resonator is configured to have a first resonance frequency range in a product having a known dielectric constant range; and said second microwave resonator is configured to have a second resonance frequency range in said product having said known dielectric constant range; wherein said first resonance frequency range does not overlap said second resonance frequency range.

21. The system according to claim 1, wherein the frequency of said transmitted electromagnetic signal is in the range of 1 to 3 GHz.

22. The system according to claim 1, wherein said non-conducting medium is liquid petroleum gas or liquid natural gas.

23. A method for determining a density of a non-conducting medium in a tank, wherein a relationship between a dielectric constant and a density of said medium is known, and wherein the density is mass per unit volume in a system comprising:
a transceiver configured to generate, transmit and receive a microwave electromagnetic signal comprising frequencies within a predetermined frequency range;
a waveguide connected to said transceiver and extending towards and into said medium, arranged to guide a transmitted electromagnetic signal towards and into said medium inside said tank, and to return an electromagnetic signal resulting from a reflection of said transmitted electromagnetic;
a first microwave resonator having a resonance frequency, and configured to reflect frequencies corresponding to a first bandwidth around said resonance frequency, said first bandwidth being smaller than and within said frequency range, said resonance frequency depending on a dielectric constant of a medium surrounding said resonator according to a known relationship;
wherein said first microwave resonator is arranged at a location along said waveguide, and configured to reflect a portion in the frequency domain, of an electromagnetic signal corresponding to said first bandwidth when said electromagnetic signal is guided along said waveguide; and
processing circuitry connected to said transceiver and configured to:
determine said resonance frequency based on a reflected portion of said signal having been reflected by the first microwave resonator, and
determine a density of said medium at the location of said first microwave resonator based on said resonance frequency, said method comprising the steps of:
generating an electromagnetic signal comprising said resonance frequency of said microwave resonator;
transmitting, with said transceiver, said electromagnetic signal along said waveguide,
receiving, with said transceiver, an electromagnetic signal reflected by said microwave resonator,
detecting a frequency range of said received electromagnetic signal, having been reflected by said microwave resonator;
determining a density of said content at said location of said microwave resonator based on said determined frequency range, and based on a known relation between the dielectric constant and density of said content.

24. The method according to claim 23, further comprising correlating a frequency range of said reflected portion of said electromagnetic signal with a resonance frequency range of said microwave resonator between a resonance frequency in air and a resonance frequency in a product having a known dielectric constant, to verify that said reflected portion of said electromagnetic signal is a result of reflection by said microwave resonator.

25. The method according to claim 23, in a system comprising
a second microwave resonator having a second resonance frequency, and configured to reflect frequencies corresponding to a second bandwidth around said second resonance frequency, said second bandwidth being smaller than and within said frequency range, said second resonance frequency being separate from the resonance frequency of said first microwave resonator, and depending on a dielectric constant of a medium surrounding said second microwave resonator according to a known relationship;

wherein said second microwave resonator is arranged at a location along said waveguide offset from said first microwave resonator, and configured to reflect a portion in the frequency domain corresponding to said second bandwidth when said electromagnetic signal is guided along said waveguide; and said method further comprises the steps of;

generating an electromagnetic signal having a frequency range comprising a resonance frequency for each of said first and said second microwave resonator;

detecting a plurality of reflected portions of a received electromagnetic signal reflected by said first and said second microwave resonator;

determining a density of said medium at each of said known positions of said microwave resonators based on said reflected portions, and based on a known relation between the dielectric constant and density of said medium.

26. The method according to claim 23, further comprising the step of determining a filling level of said medium in said tank based on a time-of-flight between said transmitted electromagnetic signal and a received electromagnetic signal reflected at a surface of said medium in said tank.

27. The method according to claim 25, further comprising the step of determining whether each of said microwave resonators is located above or below a filling level of said medium.

28. The system according to claim 1, wherein in use the first microwave resonator is immersed in the medium, the medium also filling the inside of the first microwave resonator.

29. The method according to claim 23, wherein the first microwave resonator is immersed in the medium, the medium also filling the inside of the first microwave resonator.

* * * * *